(12) United States Patent
Ignatyev et al.

(10) Patent No.: US 8,084,617 B2
(45) Date of Patent: Dec. 27, 2011

(54) IONIC LIQUIDS HAVING FLUOROALKYLTRIFLUOROBORATE ANIONS

(75) Inventors: Nikolai (Mykola) Ignatyev, Duisburg (DE); Urs Welz-Biermann, Heppenheim (DE); German Bissky, Wuppertal (DE); Helge Willner, Mühlheim/Ruhr (DE); Andriy Kucheryna, Wuppertal (DE)

(73) Assignee: Merck Patent GmbH, Darmstadt (DE)

( * ) Notice: Subject to any disclaimer, the term of this patent is extended or adjusted under 35 U.S.C. 154(b) by 801 days.

(21) Appl. No.: 10/594,966

(22) PCT Filed: Jan. 3, 2005

(86) PCT No.: PCT/EP2005/000003
§ 371 (c)(1), (2), (4) Date: Sep. 29, 2006

(87) PCT Pub. No.: WO2005/105815
PCT Pub. Date: Nov. 10, 2005

(65) Prior Publication Data
US 2007/0213538 A1    Sep. 13, 2007

(30) Foreign Application Priority Data
Apr. 2, 2004   (DE) .................... 10 2004 017 026

(51) Int. Cl.
| C07F 13/00 | (2006.01) |
|---|---|
| C07F 9/06 | (2006.01) |
| C07F 5/02 | (2006.01) |
| C07D 203/04 | (2006.01) |
| C07D 207/30 | (2006.01) |
| C07D 229/02 | (2006.01) |
| C07D 247/02 | (2006.01) |

(52) U.S. Cl. ........ 548/110; 548/405; 548/954; 548/960; 556/404; 568/6

(58) Field of Classification Search .................. None
See application file for complete search history.

(56) References Cited

U.S. PATENT DOCUMENTS
| 4,620,021 A | 10/1986 | Starzewski et al. |
| 2002/0160261 A1 | 10/2002 | Schmidt et al. |

FOREIGN PATENT DOCUMENTS
| EP | 0137389 A | 4/1985 |
| EP | 1174941 A | 1/2002 |
| EP | 1229038 A | 8/2002 |

OTHER PUBLICATIONS

McFarlane et al., Chem. Commun., 2001, 1430-1431.*
Zhi-Bin Zhou et al., "New hydrophobic ionic liquids based on perfluoroalkyltrifluoroborate anions" Journal of Fluorine Chemistry, vol. 25, No. 1, Mar. 1, 2004, pp. 471-476.
Zhi-Bin Zhou et al., "Novel electrolyte salts based on perfluoroalkyltrifluoroborate anions. 1. Synthesis and characterization" Journal of Fluorine Chemistry, vol. 123, 2003, pp. 127-131.

* cited by examiner

*Primary Examiner* — Sun Jae Loewe
(74) *Attorney, Agent, or Firm* — Millen, White, Zelano & Branigan, P.C.

(57) ABSTRACT

The invention relates to compounds of the formula (I), in which X, -$Q^1$-$Q^2$- and $R^F$ have the meaning indicated in Claim 1, as ionic liquids, and to a process for the preparation thereof.

8 Claims, 1 Drawing Sheet

IONIC LIQUIDS HAVING FLUOROALKYLTRIFLUOROBORATE ANIONS

The invention relates to ionic liquids having fluoroalkyltrifluoroborate anions, and to a process for the preparation thereof.

Ionic liquids or liquid salts are ionic species which consist of an organic cation and a generally inorganic anion. They do not contain any neutral molecules and usually have melting points of below 373 K.

The area of ionic liquids is currently being intensively researched since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227.

The properties of ionic liquids, for example melting point, thermal and electrochemical stability and viscosity, are strongly influenced by the nature of the anion. By contrast, the polarity and hydrophilicity or lipophilicity can be varied through a suitable choice of the cation/anion pair. There is, in particular, a demand for novel ionic liquids which have low viscosity.

The object of the present invention was to provide novel both thermally and electrochemically and hydrolysis-stable salt-like compounds of low viscosity which can be used as ionic liquids, and a process for the preparation thereof.

The object is achieved by the salts according to the invention having a heterocyclic cation and fluoroalkyltrifluoroborate anions according to Claim 1.

EP 1 174 941 discloses alkali-metal and ammonium salts having fluoroalkyltrifluoroborate anions, in particular lithium or tetraalkylammonium salts, which have high thermal stability and high ionic conductivity and are thus suitable for use as non-aqueous electrolytes.

Besides the fluoroalkyltrifluoroborate salts described hitherto, EP 1 229 038 also discloses tetraethylphosphonium trifluoromethyltrifluoroborate. It is additionally described that heterocyclic cations are also suitable as salts having fluoroalkylborate anions for use as electrolytes without disclosing these in greater detail. The present invention should therefore be regarded as a selection invention vis-á-vis EP 1 229 038.

The article by Zhi-Bin Zhou et al., J. Fluor. Chem. 2004, 125, 471-476, discloses the compounds 1-methyl-3-ethylimidazolium pentafluoroethyltrifluoroborate, 1-methyl-3-ethylimidazolium (n-heptafluoropropyl)trifluoroborate and 1-methyl-3-ethylimidazolium (n-nonafluorobutyl)trifluoroborate, which are hereby excluded from the scope of protection.

Surprisingly, it has been found that the compounds of the formula I lead, as described below, to particularly suitable ionic liquids since their viscosity is very low.

An important difference from the prior art is furthermore that compounds having trifluoromethyltrifluoroborate anions have always been regarded as equal to compounds having more highly perfluoroalkylated trifluoroborate anions. However, it has been shown in the course of this invention that compounds having cations of the formula I and the trifluoromethyltrifluoroborate anion are thermally unstable and thus do not meet the requirements.

The invention therefore relates to compounds of the formula I

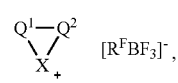

in which
X denotes $NR^1$ or $N(R^1)_2$,
$-Q^1-Q^2-$ denotes $-CHR^3-CHR^4-CHR^5-CHR^6-$,
   $-CR^2=CR^3-CR^4=CR^5-CR^6=$ or
   $-CR^7=CR^8-NR^{10}-CR^9=$,
$R^1$ in each case, independently of one another, denotes alkyl having 1-10 C atoms or $-(CH_2)-R^{11}$,
$R^2$-$R^6$ denote hydrogen or alkyl having 1-10 C atoms,
$R^7$-$R^9$ denote hydrogen, alkyl having 1-10 C atoms or aryl,
$R^{10}$ denotes alkyl having 2-10 C-atoms or $-(CH_2)-R^{11}$,
$R^{11}$ denotes perfluorinated or partially fluorinated alkyl having 1-8 C atoms,
$R^F$ denotes perfluorinated alkyl having 2-8 C atoms, and
aryl denotes phenyl, fluorinated phenyl, or phenyl or fluorinated phenyl which is substituted by alkyl having 1-8 C atoms.

The $C_1$-$C_{10}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl or decyl. The alkyl groups may, if desired, be fully or partially fluorinated.

Aryl denotes phenyl or fluorinated phenyl ($C_6F_{5-x} H_x$, where x=0-4), which may be mono- or polysubstituted by $C_1$- to $C_8$-alkyl, for example methylphenyl, (methyl)tetrafluorophenyl, ethylphenyl, propylphenyl, isopropylphenyl, tert-butylphenyl, pentylphenyl, hexylphenyl, heptylphenyl, octylphenyl, (trifluoromethyl)phenyl, (trifluoromethyl)tetrafluorophenyl, (pentafluoroethyl)phenyl, (heptafluoropropyl)phenyl, (heptafluoropropyl)tetrafluorophenyl, dimethylphenyl, diethylphenyl, di(tert-butyl)phenyl, tri(tertbutyl)phenyl, trimethylphenyl or bis(trifluoromethyl)phenyl.

Cycloalkyl having 3-7 C atoms denotes cyclopropyl, cyclobutyl, cyclopentyl, cyclohexyl or cycloheptyl, which may optionally be substituted by F, Cl or Br, in particular F.

In accordance with the invention, preference is given to a group of compounds of the formula I in which X denotes $N(R^1)_2$ and $-Q^1-Q^2-$ denotes $-CHR^3-CHR^4-CHR^5-CHR^6$, which can be depicted by the formula Ia

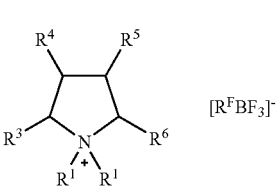

and in which the substituents $R^F$, $R^1$ and $R^3$ to $R^6$ are as defined for the formula I.

Compounds of the formula Ia are distinguished, in particular, by their high electrochemical stability. This is confirmed by the cyclic voltamogram (FIG. 1) of the compound N-methyl-N-butylpyrrolidinium pentafluoroethyltrifluoroborate.

$R^F$ in the formula Ia is preferably pentafluoroethyl, heptafluoropropyl or nonafluorobutyl. $R^1$ in the formula Ia is preferably $C_1$-$C_{10}$-alkyl. The substituents $R^3$ to $R^6$ in the formula Ia are preferably hydrogen. Particular preference is given to compounds of the formula Ia in which the two substituents $R^1$ are different.

In accordance with the invention, preference is given to a group of compounds of the formula I in which X denotes $NR^1$ and -$Q^1$-$Q^2$- denotes —$CR^2$=$CR^3$—$CR^4$=$CR^5$—$CR^6$=, which can be depicted by the formula Ib

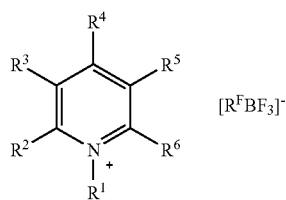

and where the substituents $R^F$, $R^1$ to $R^6$ are as defined for the formula I.

$R^F$ in the formula Ib is preferably pentafluoroethyl, heptafluoropropyl or nonafluorobutyl, particularly preferably pentafluoroethyl. $R^1$ in the formula Ib is preferably $C_1$-$C_{10}$-alkyl. $R^2$ to $R^6$ in the formula Ib are preferably hydrogen or $C_1$-$C_4$-alkyl.

In accordance with the invention, preference is given to a group of compounds of the formula I in which X denotes $NR^1$ and -$Q^1$-$Q^2$- denotes —$CR^7$=$CR^8$—$NR^{10}$—$CR^9$=, which can be depicted by the formula Ic

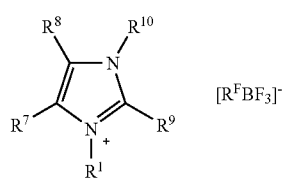

and where the substituents $R^F$, $R^1$ and $R^7$ to $R^{10}$ are as defined for the formula I.

$R^F$ in the formula Ic is preferably pentafluoroethyl, heptafluoropropyl or nonafluorobutyl. $R^1$ and $R^{10}$ in the formula Ic are preferably $C_1$-$C_{10}$-alkyl. The substituents $R^7$ and $R^8$ are preferably hydrogen or $C_1$-$C_4$-alkyl. Particular preference is given to compounds of the formula Ic in which the substituents $R^1$ and $R^{10}$ are different.

Particular preference is given to the following compounds according to the invention:
N-methyl-N-butylpyrrolidinium pentafluoroethyltrifluoroborate,
N-methyl-N-hexylpyrrolidinium pentafluoroethyltrifluoroborate,
N-methyl-N-octylpyrrolidinium pentafluoroethyltrifluoroborate,
1-methyl-3-butylimidazolium pentafluoroethyltrifluoroborate,
1-methyl-3-hexylimidazolium pentafluoroethyltrifluoroborate,
or 1,2-dimethyl-3-butylimidazolium pentafluoroethyltrifluoroborate.

The compounds of the formula I according to the invention having the special feature of low viscosity are particularly suitable for use as ionic liquid, with use of the ionic liquids in turn preferably as solvent, extractant or heat-transfer medium in the foreground.

The compounds of the formula I can be synthesised by reaction of the corresponding halide of the compounds of the formula I with an alkali-metal, alkaline-earth metal or ammonium perfluoroalkyltrifluoroborate, prepared by the process of Chambers et al., J. Am. Soc. 82 (1960), 5298 or EP 1 229 038.

The invention likewise relates to a process for the preparation of the compounds of the formula I, as described above, as a one-pot synthesis, characterised in that
in the first step, a compound of the formula II $$(R^F)_3P=NSi(R^{12})_3 \qquad \text{II,}$$

in which
$R^F$ in each case, independently of one another, denotes perfluorinated alkyl having 2-8 C atoms, preferably perfluorinated $C_2$-$C_4$-alkyl, where all three substituents $R^F$ are identical, and
$R^{12}$ in each case, independently of one another, denotes alkyl having 1-8 C atoms, alkoxy having 1-8 C atoms, cycloalkyl having 3-7 C atoms, halogen (F, Cl or Br) or aryl,
is reacted with a fluoride of the formula III $$MF \qquad \text{III,}$$

in which
M is ammonium, alkali metal or alkaline earth metal or a metal from group 11 or 12,
and a boric acid ester of the formula IV $$B(OR^{13})_3 \qquad \text{IV,}$$

in which
$R^{13}$ in each case, independently of one another, denotes alkyl having 1-8 C atoms or aryl,
and the resultant salt of the formula V $$M[R^F B(OR^{13})_3] \qquad \text{V,}$$

in which M, $R^F$ and $R^{13}$ have one of the above-mentioned meanings,
is reacted, in the second step, with HF,
and the resultant salt of the formula VI $$M[R^F BF_3] \qquad \text{VI,}$$

in which $R^F$ is as defined above,
is reacted, in the third step, with a compound of the formula VII

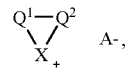

in which X and -$Q^1$-$Q^2$- are as defined for the formula I in Claims 1 to 4, and $A^-$ denotes alkylsulfate, alkylsulfonate, trifluoromethanesulfonate, tetrafluoroborate, acetate, trifluoroacetate, bis(perfluoroalkyl)phosphinate, $F^-$, $HF_2^-$, $Cl^-$, $Br^-$ or $I^-$.

Compounds of the formula II $$(R^F)_3P=NSi(R^{12})_3 \qquad \text{II,}$$

in which $R^F$ in each case, independently of one another, denotes perfluorinated alkyl having 2-8 C atoms, preferably perfluorinated $C_2$-$C_4$-alkyl, where all three substituents $R^F$ are identical, and $R^{12}$ in each case, independently of one another, denotes alkyl having 1-8 C atoms, alkoxy having 1-8 C atoms, cycloalkyl having 3-7 C atoms, halogen (F, Cl or Br) or aryl, are novel.

Similar compounds are known from EP 0 250 999 and EP 0 137 389, in particular (phenyl)$_3$P=NSi(CH$_3$)$_3$.

The N-silyltris(perfluoroalkyl)phosphazenes (synonymous names are N-silyltris(perfluoroalkyl)iminophosphoranes and N-silyltris(perfluoroalkyl)-phosphinimines) employed in accordance with the invention are to be regarded as a selection with respect to EP 0 250 999.

Preference is given to compounds of the formula II in which $R^F$ is a perfluorinated alkyl having 2 to 4 C atoms. Preference is likewise given to compounds of the formula II in which $R^{12}$ is an alkyl having 1-4 C atoms.

Particularly preferred compounds are compounds of the formula II in which $R^F$ is a perfluorinated alkyl having 2-4 C atoms and in which $R^{12}$ is alkyl having 1-4 C atoms, for example (C$_2$F$_5$)$_3$P=NSi(CH$_3$)$_3$, (C$_3$F$_7$)$_3$P=NSi(CH$_3$)$_3$, (C$_4$F$_9$)$_3$P=NSi(CH$_3$)$_3$, (C$_2$F$_5$)$_3$P=NSi(C$_2$H$_5$)$_3$, (C$_3$F$_7$)$_3$P=NSi(C$_2$H$_5$)$_3$, (C$_4$F$_9$)$_3$P=NSi(C$_2$H$_5$)$_3$, (C$_2$F$_5$)$_3$P=NSi(C$_3$H$_7$)$_3$, (C$_3$F$_7$)$_3$P=NSi(C$_3$H$_7$)$_3$, (C$_4$F$_9$)$_3$P=NSi(C$_3$H$_7$)$_3$, (C$_2$F$_5$)$_3$P=NSi(C$_4$H$_9$)$_3$, (C$_3$F$_7$)$_3$P=NSi(C$_4$H$_9$)$_3$ or (C$_4$F$_9$)$_3$P=NSi(C$_4$H$_9$)$_3$.

Very particularly preferred compounds are (C$_2$F$_5$)$_3$P=NSi(CH$_3$)$_3$ and (C$_4$F$_9$)$_3$P=NSi(CH$_3$)$_3$.

Suitable for the trifluoromethylation of organic compounds or for the synthesis of the known trifluoromethyltrifluoroborate anion are the compounds (CF$_3$)$_3$P=NSi(CH$_3$)$_3$, (CF$_3$)$_3$P=NSi(C$_2$H$_5$)$_3$, (CF$_3$)$_3$P=NSi(C$_3$H$_7$)$_3$ and (CF$_3$)$_3$P=NSi(C$_4$H$_9$)$_3$, in particular the compound (CF$_3$)$_3$P=NSi(CH$_3$)$_3$.

Compounds of the formula II are obtained by reaction of a difluorotris(perfluoroalkyl)phosphorane $(R^F)_3PF_2$ with a silylamine[$(R^{12})_3$Si]$_2$NH or a silylamide[$(R^{12})_3$Si]$_2$N$^-$K$^+$, where the substituents $R^F$ and $R^{12}$ are as defined above and K$^+$ denotes Li$^+$, Na$^+$, K$^+$, R$^+$, Mg$^{2+}$, Ca$^{2+}$ or Cu$^+$ (charge neutrality should be observed here in accordance with general understanding), but where compounds of the formula II in which $R^F$ may, in addition to the above-mentioned meaning, also denote trifluoromethyl can also be prepared by this process.

The reaction is advantageously carried out without a solvent, where temperatures of 10-150° C., preferably 50-120° C., particularly preferably 60-90° C., are suitable.

However, the reaction can alternatively also take place in solvents at temperatures of between 10 and 150° C. Suitable solvents here are benzene, hexane, acetonitrile, dioxane and dimethoxyethane.

N-Silyltris(perfluoroalkyl)phosphinimines are stable liquids which are in some cases also air-stable. Perfluoroalkyl here denotes a perfluoroalkyl group having 1 to 8 C atoms. They are highly suitable as perfluoroalkylating agents. On addition of strong bases, perfluoroalkyl anions are liberated which are able to react with a very wide variety of electrophiles, for example with carbonyl groups.

N-Silyltris(perfluoroalkyl)phosphinimines of the formula II are particularly suitable in accordance with the invention for the generation of perfluoroalkyltrifluoroborate anions having 1 to 8 C atoms and for the synthesis of compounds of the formula I as described above.

For the synthesis of the compounds of the formula I, a compound of the formula II

   II, as described above, is reacted, in a first step, with a fluoride of the formula III

MF   III, in which

M is ammonium, alkali metal or alkaline earth metal or a metal from group 11 or 12, and a boric acid ester of the formula IV

   IV, in which $R^{13}$ in each case, independently of one another, denotes alkyl having 1-8 C atoms or aryl, to give the salt of the formula V

   V.

Suitable compounds of the formula III are NaF, KF, RbF, CsF, MgF$_2$, tetraalkylammonium fluoride, AgF and CdF$_2$. Particular preference is given to the use of KF.

Suitable boric acid esters of the formula IV are trimethyl borate, triethyl borate, tripropyl borate, tri(tert-butyl)borate and triphenyl borate, in particular trimethyl borate.

The reaction in the first step is carried out in an organic solvent at temperatures between 0 and 120° C., preferably between 20 and 100° C., particularly preferably between 40 and 80° C. and preferably under a protective-gas atmosphere. Suitable solvents are dimethoxyethane, tetrahydrofuran, diglyme and triglyme. Particular preference is given to the use of dimethoxyethane.

The resultant salt of the formula V

   V, in which $R^F$ and $R^{13}$ have one of the above-mentioned meanings, and M is ammonium, alkali metal or alkaline earth metal or a metal from group 11 or 12, can be reacted further with HF without further purification as a one-pot reaction.

It is a general understanding here that it is possible, in the course of the one-pot synthesis according to the invention, firstly to distil off the solvent used and to take up the residue again in a solvent. This operation does not correspond to isolation. For example, the solvent tetrahydrofuran cannot be employed in the reaction with HF since it would likewise react with HF. A change of the solvent is therefore inevitably necessary for successful conversion to a compound of the formula VI.

The reaction with HF is preferably carried out in the solvent of the first step, with the exception of tetrahydrofuran, at temperatures of −10 to 60° C., preferably at 0 to 40° C., particularly preferably at room temperature. Without isolation, if desired after prior removal of the solvent by distillation, the resultant salt of the formula VI

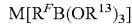   VI, in which $R^F$ is as defined above, and

M is ammonium, alkali metal or alkaline earth metal or a metal from group 11 or 12, is reacted, in the third step, with a compound of the formula VIII

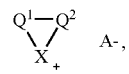   VII in which X and -Q$^1$-Q$^2$- are as defined above for the formula I, and A$^-$ denotes alkylsulfate, alkylsulfonate, trifluoromethanesulfonate, tetrafluoroborate, acetate, trifluoroacetate, bis(perfluoroalkyl)phosphinate, F$^-$, HF$_2^-$, Cl$^-$, Br$^-$ or I$^-$, at temperatures between 0 and 100° C., preferably at 10° C.-50° C., particularly preferably at room temperature.

This third reaction step can be carried out in water or a mixture of water and an organic solvent, for example dimethoxyethane, tetrahydrofuran, diglyme or triglyme, or in the pure organic solvent.

The third reaction step inevitably gives a mixture of the salts of the formula I according to the invention, as defined above, also including the sub-formulae Ia, Ib and Ic, with salts of the formulae VIII, IX and X

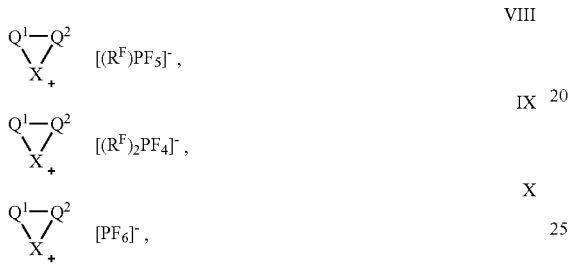

where X, -Q$^1$-Q$^2$- and R$^F$ have the same meaning as for the salts of the formula I or the sub-formulae Ia, Ib and Ic, forming VIIIa, VIIIb, VIIIc, IXa, IXb, IXc, Xa, Xb and Xc.

The compound of the formula II is therefore capable of releasing one, two or all three perfluoroalkyl groups bonded to P in the reaction.

The resultant mixture can comprise 50-75 mol % of compounds of the formula I and 25-50 mol % of compounds of the formulae VIII, IX and X. The mixture of the phosphate salts of the formulae VIII, IX and X can consist of 0-75 mol % of a compound of the formula VIII, 0-50 mol % of a compound of the formula IX and 0-25 mol % of a compound of the formula X.

The mixture of the salts of the formulae I, VIII, IX and/or X is likewise suitable in accordance with the invention for use as ionic liquid. Separation of the salts is possible by known methods, in particular by the methods indicated in the examples.

However, the first two steps of the process according to the invention should also be understood as meaning that salts of the formula VI $$M[R^F BF_3] \quad VI,$$

in which R$^F$ is as defined above, and
M is ammonium, alkali metal or alkaline earth metal or a metal from group 11 or 12, can be prepared specifically in a novel process with the aid of these reactions, where the substituent R$^F$ may also encompass trifluoromethyl in this respect. In particular, the following compounds can be synthesised by a process of this type:
K[CF$_3$BF$_3$], K[C$_2$F$_5$BF$_3$], K[C$_3$F$_7$BF$_3$], K[C$_4$F$_9$BF$_3$], Rb[C$_2$F$_5$BF$_3$],
Rb[C$_4$F$_9$BF$_3$], Ag[C$_2$F$_5$BF$_3$], Ag[C$_4$F$_9$BF$_3$] or Cs[C$_2$F$_5$BF$_3$].

The complete disclosure content of all applications, patents and publications mentioned above and below is incorporated into this application by way of reference.

Even without further comments, it is assumed that a person skilled in the art will be able to utilise the above description in the broadest scope. The preferred embodiments and examples should therefore merely be regarded as descriptive disclosure which is absolutely not limiting in any way.

The NMR spectra were measured on solutions in deuterated solvents at 20° C. in a Bruker Avance 250 spectrometer. The measurement frequencies of the various nuclei are: $^1$H, 250.13 MHz, $^{19}$F: 235.357 MHz and $^{31}$P: 101.254 MHz. The referencing method is indicated separately for each spectrum or each data set.

EXAMPLE 1

Synthesis of the Starting Materials

A) Synthesis of N-trimethylsilyltris(pentafluoroethyl)phosphazene

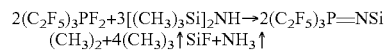

Figure 1:
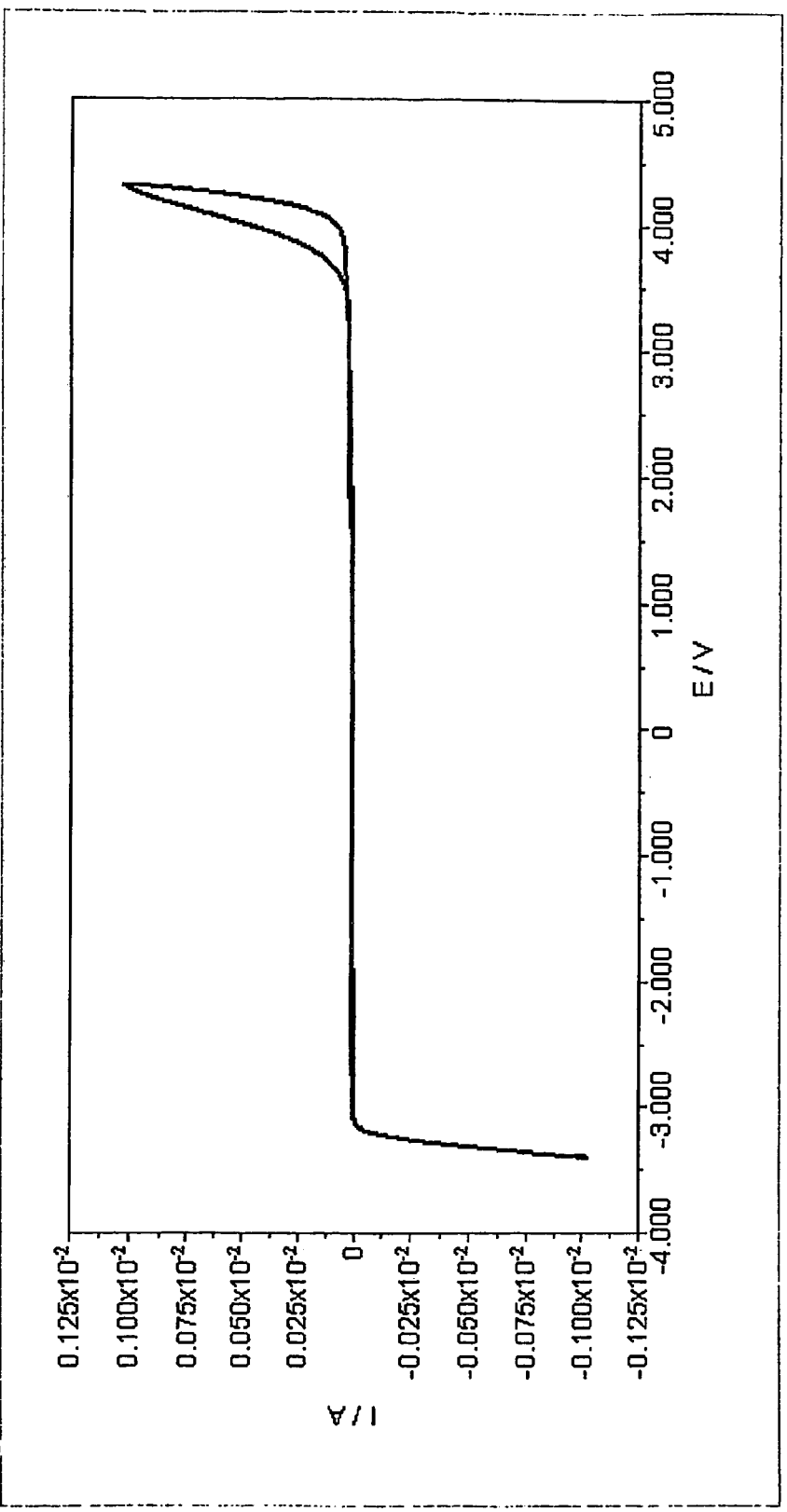
FIG. 1 is a cyclic voltamogram showing electrochemical stability.

210.4 g (0.49 mol) of tris(pentafluoroethyl)difluorophosphorane are mixed with 123.0 g (0.76 mol) of bis(trimethylsilyl)amine in a corresponding apparatus and stirred for 3 hours at oil-bath temperatures of 80°-90° C. The resultant N-trimethylsilyltris(pentafluoroethyl)phosphazene can be reacted further without further purification. In order to characterise the compound, it is distilled off at atmospheric pressure, giving 204.2 g of N-trimethylsilyltris (pentafluoroethyl) phosphazene having a boiling point of 143-145° C., corresponding to a yield of 87%.

$^{19}$F NMR, ppm (CDCl$_3$, internal reference: CCl$_3$F): −79.08 m (CF$_3$), −118.59 dm (CF$_2$), $^2$J$_{P,F}$=85 Hz.

$^1$H NMR, ppm (CDCl$_3$, reference TMS): 0.07 br.s (CH$_3$).

$^{31}$P NMR, ppm (CDCl$_3$, reference: 85% H$_3$PO$_4$): −41.07 hep, $^2$J$_{P,F}$=85 Hz.

B) N-Trimethylsilyltris(nonafluorobutyl)phosphazene

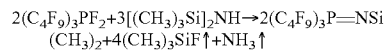

Analogously to Example 1A), 72.0 g (99.2 mmol) of tris (nonafluorobutyl)difluorophosphorane are reacted with 24.9 g (154.3 mmol) of bis(trimethylsilyl)amine, giving 64.0 g of N-trimethylsilyltris(nonafluorobutyl)phosphazene, corresponding to a yield of 83.2%.

B.p.: 108-110° C. at 2.27 kPa.

$^{19}$F NMR, ppm (without solvent, acetonitrile-D$_3$ film, internal reference: CCl$_3$F): −82.38 t (CF$_3$), −113.72 dm (CF$_2$), −118.92 m (CF$_2$), −126.93 m (CF$_2$), $^4$J$_{F,F}$=9.1 Hz, $^2$J$_{P,F}$=87 Hz.

$^1$H NMR, ppm (without solvent, acetonitrile-D$_3$ film, external reference: TMS): −0.70 br.s (CH$_3$).

$^{31}$P NMR, ppm (without solvent, acetonitrile-D$_3$ film, reference: 85% H$_3$PO$_4$): −42.09 hep, $^2$J$_{P,F}$=87 Hz.

EXAMPLE 2

Synthesis of 1-methyl-3-butylimidazolium pentafluoroethyltrifluoroborate

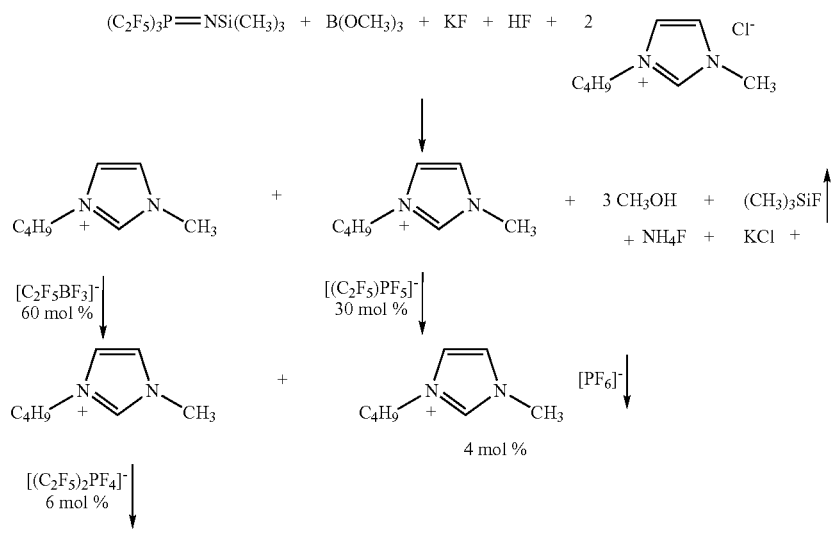

3.32 g (57.1 mmol) of spray-dried KF and 10.4 g (100 mmol) of trimethyl borate are dissolved in 100 ml of dry 1,2-dimethoxyethane. 30.0 g (63.1 mmol) of N-trimethylsilyltris(pentafluoroethyl)phosphazene, $(C_2F_5)_3P=NSi(CH_3)_3$, are added dropwise to this solution at room temperature under a protective gas. The reaction mixture is heated to 60° C. with stirring and stirred at this temperature for one hour until the KF has completely dissolved. The solvent is distilled off, and the oily residue is taken up in 100 ml of 1,2-dimethoxyethane. 20.0 g (1 mol) of HF are added to this solution with cooling of the reaction mixture using an ice bath. After the mixture has been stirred at room temperature for 3 hours, the excess acid HF is distilled off, and the residue is taken up in 200 ml of water. 25.2 g (144.27 mmol) of 1-methyl-3-butylimidazolium chloride in 50 ml of water are added to this solution. The lower phase, which contains the mixture of the novel imidazolium salts, is separated off.

Drying at 7 Pa and 50° C. gives a mixture of the salts 1-methyl-3-butylimidazolium pentafluoroethyltrifluoroborate (about 60 mol %), 1-methyl-3-butylimidazolium (pentafluoroethyl)pentafluorophosphate (about 30 mol %), 1-methyl-3-butylimidazolium bis(pentafluoroethyl)tetrafluorophosphate (about 6 mol %) and 1-methyl-3-butylimidazolium hexafluorophosphate (about 4 mol %).

If, by contrast, the lower phase is washed a number of times with 100 ml of water, the (pentafluoroethyl)pentafluorophosphate and the other phosphates are separated off from the pentaethyltrifluoroborate. The borate is then dried at 7 Pa and 50° C.

13.7 g of 1-methyl-3-butylimidazolium pentafluoroethyltrifluoroborate are obtained as a liquid, corresponding to a yield of 70.2%, based on KF.

$^{11}$B NMR: ppm (acetonitrile-D$_3$; external reference: BF$_3$.OEt$_2$): −0.60 qt; $J^1_{B,F}$=40.9 Hz; $J^2_{B,F}$=20.3 Hz.

$^{19}$F NMR: ppm (acetonitrile-D$_3$; internal reference: CCl$_3$F): −83.20 q (CF$_3$); −135.98 q (CF$_2$); −152.84 q,q (BF$_3$); $^1J_{B,F}$=41 Hz; $^2J_{B,F}$=19.6 Hz; $^4J_{F,F}$=5.0 Hz.

$^1$H NMR: ppm (acetonitrile-D$_3$; reference: TMS): 0.95 t (CH$_3$); 1.34 m (CH$_2$); 1.82 t,t (CH$_2$); 3.83 s (CH$_3$); 4.13 t (CH$_2$); 7.33 d,d (CH); 7.36 d,d (CH); 8.39 br.s (CH); $^3J_{H,H}$=7.3 Hz; $^3J_{H,H}$=6.8 Hz; $J_{H,H}$=1.8 Hz.

The phosphates can be isolated from the aqueous phase by known methods.

1-Methyl-3-butylimidazolium (pentafluoroethyl)pentafluorophosphate $^{19}$F NMR (CD$_3$CN: internal reference CCl$_3$F): −70.14 d,d,m (PF$_4$); −73.50 d,quin (PF); −82.46 quin,m (CF$_3$); −118.79 d,quin (CF$_2$); $^1J_{P,F}$=827 Hz; $^1J_{P,F}$=720 Hz; $^2J_{P,F}$=91 Hz; $^2J_{F,F}$=47 Hz; $^3J_{F,F}$=9.2 Hz; $^4J_{F,F}$=7.6 Hz.

1-Methyl-3-butylimidazolium bis(pentafluoroethyl)tetrafluorophosphate $^{19}$F NMR (CD$_3$CN, internal reference: CCl$_3$F): −71.59 d,m (PF$_4$); −82.27 quin,d,t (2CF$_3$); −118.99 d,quin,q (2CF$_2$); $^1J_{P,F}$=916 Hz; $^2J_{P,F}$=100 Hz; $^3J_{P,F}$=2.4 Hz; $^3J_{F,F}$=9.2 Hz; $^3J_{F,F}$=1.1 Hz; $^4J_{F,F}$=7.4 Hz.

1-Methyl-3-butylimidazolium hexafluorophosphate $^{19}$F NMR (CD$_3$CN, internal reference: CCl$_3$F): −71.53 d (PF$_4$); $^1J_{P,F}$=707 Hz.

The following mixtures and also isolated compounds are prepared analogously to this example:

A) 1,2-Dimethyl-3-butylimidazolium pentafluoroethyltrifluoroborate isolated or mixed with 1,2-dimethyl-3-butylimidazolium (pentafluoroethyl)pentafluorophosphate and/or 1,2-dimethyl-3-butylimidazolium bis(pentafluoroethyl)tetrafluorophosphate and/or 1,2-dimethyl-3-butylimidazolium hexafluorophosphate;

B) 1-Methyl-3-ethylylimidazolium pentafluoroethyltrifluoroborate isolated or mixed with 1-methyl-3-ethylimidazolium (pentafluoroethyl)pentafluorophosphate and/or 1-methyl-3-ethylimidazolium bis(pentafluoroethyl)tetrafluorophosphate and/or 1-methyl-3-ethylimidazolium hexafluorophosphate;

C) 1-Methyl-3-i-propylimidazolium pentafluoroethyltrifluoroborate isolated or mixed with 1-methyl-3-i-propylimidazolium (pentafluoroethyl)pentafluorophosphate and/or 1-methyl-3-i-propylimidazolium bis(pentafluoroethyl)tetrafluorophosphate and/or 1-methyl-3-i-propylimidazolium hexafluorophosphate;

D) 1-Methyl-3-n-propylimidazolium pentafluoroethyltrifluoroborate isolated or mixed with 1-methyl-3-n-propylimidazolium (pentafluoroethyl)pentafluorophosphate and/or 1-methyl-3-n-propylimidazolium bis(pentafluoroethyl)tetrafluorophosphate and/or 1-methyl-3-n-propylimidazolium hexafluorophosphate;

E) 1-Methyl-3-pentylimidazolium pentafluoroethyltrifluoroborate isolated or mixed with 1-methyl-3-pentylimidazolium (pentafluoroethyl)pentafluorophosphate and/or 1-methyl-3-pentylimidazolium bis(pentafluoroethyl)tetrafluorophosphate and/or 1-methyl-3-pentylimidazolium hexafluorophosphate;

F) 1-Methyl-3-hexylimidazolium pentafluoroethyltrifluoroborate isolated or mixed with 1-methyl-3-hexylimidazolium (pentafluoroethyl)pentafluorophosphate and/or 1-methyl-3-hexylimidazolium bis(pentafluoroethyl)tetrafluorophosphate and/or 1-methyl-3-hexylimidazolium hexafluorophosphate;

G) 1-Methyl-3-heptylimidazolium pentafluoroethyltrifluoroborate isolated or mixed with 1-methyl-3-heptylimidazolium (pentafluoroethyl)pentafluorophosphate and/or 1-methyl-3-heptylimidazolium bis(pentafluoroethyl)tetrafluorophosphate and/or 1-methyl-3-heptylimidazolium hexafluorophosphate;

H) 1-Methyl-3-octylimidazolium pentafluoroethyltrifluoroborate isolated or mixed with 1-methyl-3-octylimidazolium (pentafluoroethyl)pentafluorophosphate and/or 1-methyl-3-octylimidazolium bis(pentafluoroethyl)tetrafluorophosphate and/or 1-methyl-3-octylimidazolium hexafluorophosphate;

I) 1-Methyl-3-nonylimidazolium pentafluoroethyltrifluoroborate isolated or mixed with 1-methyl-3-nonylimidazolium (pentafluoroethyl)pentafluorophosphate and/or 1-methyl-3-nonylimidazolium bis(pentafluoroethyl)tetrafluorophosphate and/or 1-methyl-3-nonylimidazolium hexafluorophosphate;

J) 1-Methyl-3-decylimidazolium pentafluoroethyltrifluoroborate isolated or mixed with 1-methyl-3-decylimidazolium (pentafluoroethyl)pentafluorophosphate and/or 1-methyl-3-decylimidazolium bis(pentafluoroethyl)tetrafluorophosphate and/or 1-methyl-3-decylimidazolium hexafluorophosphate;

K) 1,2-dimethyl-3-ethylylimidazolium pentafluoroethyltrifluoroborate isolated or mixed with 1,2-dimethyl-3-ethylimidazolium (pentafluoroethyl)pentafluorophosphate and/or 1,2-dimethyl-3-ethylimidazolium bis(pentafluoroethyl)tetrafluorophosphate and/or 1,2-dimethyl-3-ethylimidazolium hexafluorophosphate;

L) 1,2-dimethyl-3-i-propylimidazolium pentafluoroethyltrifluoroborate isolated or mixed with 1,2-dimethyl-3-i-propylimidazolium (pentafluoroethyl)pentafluorophosphate and/or 1,2-dimethyl-3-i-propylimidazolium bis(pentafluoroethyl)tetrafluorophosphate and/or 1,2-dimethyl-3-i-propylimidazolium hexafluorophosphate;

M) 1,2-Dimethyl-3-n-propylimidazolium pentafluoroethyltrifluoroborate isolated or mixed with 1,2-dimethyl-3-n-propylimidazolium (pentafluoroethyl)pentafluorophosphate and/or 1,2-dimethyl-3-n-propylimidazolium bis(pentafluoroethyl)tetrafluorophosphate and/or 1,2-dimethyl-3-n-propylimidazolium hexafluorophosphate;

N) 1,2-dimethyl-3-pentylimidazolium pentafluoroethyltrifluoroborate isolated or mixed with 1,2-dimethyl-3-pentylimidazolium (pentafluoroethyl)pentafluorophosphate and/or 1,2-dimethyl-3-pentylimidazolium bis(pentafluoroethyl)tetrafluorophosphate and/or 1,2-dimethyl-3-pentylimidazolium hexafluorophosphate;

O) 1,2-Dimethyl-3-hexylimidazolium pentafluoroethyltrifluoroborate isolated or mixed with 1,2-dimethyl-3-hexylimidazolium (pentafluoroethyl)pentafluorophosphate and/or 1,2-dimethyl-3-hexylimidazolium bis(pentafluoroethyl)tetrafluorophosphate and/or 1,2-dimethyl-3-hexylimidazolium hexafluorophosphate;

P) 1,2-Dimethyl-3-heptylimidazolium pentafluoroethyltrifluoroborate isolated or mixed with 1,2-dimethyl-3-heptylimidazolium (pentafluoroethyl)pentafluorophosphate and/or 1,2-dimethyl-3-heptylimidazolium bis(pentafluoroethyl)tetrafluorophosphate and/or 1,2-dimethyl-3-heptylimidazolium hexafluorophosphate;

Q) 1,2-Dimethyl-3-octylimidazolium pentafluoroethyltrifluoroborate isolated or mixed with 1,2-dimethyl-3-octylimidazolium (pentafluoroethyl)pentafluorophosphate and/or 1,2-dimethyl-3-octylimidazolium bis(pentafluoroethyl)tetrafluorophosphate and/or 1,2-dimethyl-3-octylimidazolium hexafluorophosphate;

R) 1,2-Dimethyl-3-nonylimidazolium pentafluoroethyltrifluoroborate isolated or mixed with 1,2-dimethyl-3-nonylimidazolium (pentafluoroethyl)pentafluorophosphate and/or 1,2-dimethyl-3-nonylimidazolium bis(pentafluoroethyl)tetrafluorophosphate and/or 1,2-dimethyl-3-nonylimidazolium hexafluorophosphate;

S) 1,2-Dimethyl-3-decylimidazolium pentafluoroethyltrifluoroborate isolated or mixed with 1,2-dimethyl-3-decylimidazolium (pentafluoroethyl)pentafluorophosphate and/or 1,2-dimethyl-3-decylimidazolium bis(pentafluoroethyl)tetrafluorophosphate and/or 1,2-dimethyl-3-decylimidazolium hexafluorophosphate;

T) 1-Ethyl-3-butylimidazolium pentafluoroethyltrifluoroborate isolated or mixed with 1-ethyl-3-butylimidazolium (pentafluoroethyl)pentafluorophosphate and/or 1-ethyl-3-butylimidazolium bis(pentafluoroethyl)tetrafluorophosphate and/or 1-ethyl-3-butylimidazolium hexafluorophosphate.

EXAMPLE 3

Synthesis of N-methyl-N-butylpyrrolidinium pentafluoroethyltrifluoroborate

 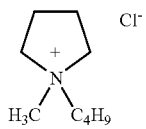

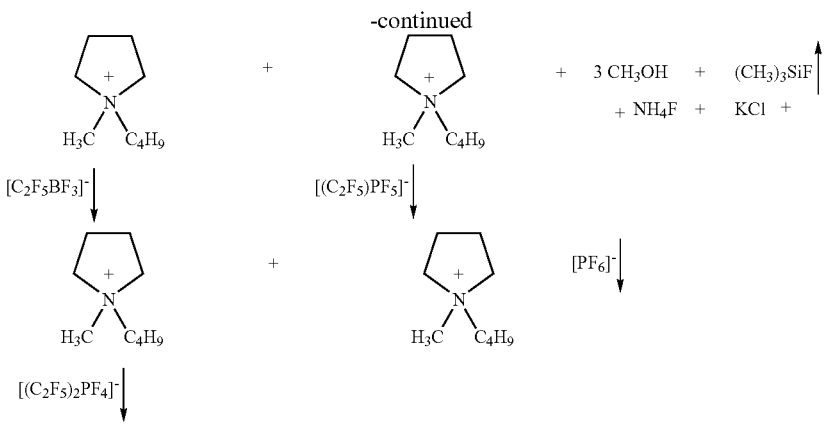

1.67 g (28.7 mmol) of spray-dried KF, 6.24 g (60.1 mmol) of methyl borate, 15.0 g (31.6 mmol) of N-trimethylsilyltris(pentafluoroethyl)phosphazene, 15 g (0.75 mol) of HF and 11.5 g (64.7 mmol) of N-Methyl-N-butylpyrrolidinium chloride are reacted analogously to Example 2.

The lower phase is separated from the aqueous phase analogously to Example 2 and washed with small portions of water. It consists of the mixture of the salts N-methyl-N-butylpyrrolidinium pentafluoroethyltrifluoroborate and N-methyl-N-butylpyrrolidinium (pentafluoroethyl)pentafluorophosphate and/or N-methyl-N-butylpyrrolidinium bis(pentafluoroethyl)tetrafluorophosphate and/or N-methyl-N-butylpyrrolidinium hexafluorophosphate. This solid lower phase is taken up in 40 ml of ethanol, and 100 ml of water are added, after which N-methyl-N-butylpyrrolidinium pentafluoroethyltrifluoroborate precipitates. This recrystallisation is carried out a further three times for further purification of the phosphates, and the solid is then dried under reduced pressure at 7 Pa and 50° C., giving 6.9 g of N-methyl-N-butylpyrrolidinium pentafluoroethyltrifluoroborate, corresponding to a yield of 73.1%, based on KF.

B.p.: 79-81° C.

$^{11}$B NMR: ppm (acetonitrile-$D_3$; external reference: $BF_3.OEt_2$): −0.47 tq; $J^1_{B,F}$=40.9 Hz; $J^2_{B,F}$=20.7 Hz.

$^{19}$F NMR: ppm (acetonitrile-$D_3$; internal reference: $CCl_3F$): −83.20 q ($CF_3$); −136.00 q ($CF_2$); −152.90 q,q ($BF_3$); $^1J_{B,F}$=41 Hz; $^2J_{B,F}$=19.6 Hz;

$^4J_{F,F}$=4.6 Hz.

$^1$H NMR: ppm (acetonitrile-$D_3$; reference: TMS): 0.98 t ($CH_3$); 1.38 t,q ($CH_2$); 1.73 m ($CH_2$); 2.17 m ($2CH_2$); 2.94 s ($CH_3$); 3.40 m ($2CH_2$); 3.22 t,t ($CH_2$); $^3J_{H,H}$=7.4 Hz; $^3J_{H,H}$=4.3 Hz; $^2J_{H,H}$=4.1 Hz.

N-Methyl-N-butylpyrrolidinium (pentafluoroethyl)pentafluorophosphate and the other phosphates can be isolated from the aqueous ethanolic phase by known methods.

The following mixtures and also isolated compounds are prepared analogously to this example:

A) N-Methyl-N-ethylpyrrolidinium pentafluoroethyltrifluoroborate isolated or mixed with N-methyl-N-ethylpyrrolidinium (pentafluoroethyl)pentafluorophosphate and/or N-methyl-N-ethylpyrrolidinium bis(pentafluoroethyl)tetrafluorophosphate and/or N-methyl-N-ethylpyrrolidinium hexafluorophosphate;

B) N-Methyl-N-1-propylpyrrolidinium pentafluoroethyltrifluoroborate isolated or mixed with N-methyl-N-1-propylpyrrolidinium (pentafluoroethyl)pentafluorophosphate and/or N-methyl-N-1-propylpyrrolidinium bis(pentafluoroethyl)tetrafluorophosphate and/or N-methyl-N-1-propylpyrrolidinium hexafluorophosphate;

C) N-Methyl-N-propylpyrrolidinium pentafluoroethyltrifluoroborate isolated or mixed with N-methyl-N-propylpyrrolidinium (pentafluoroethyl)pentafluorophosphate and/or N-methyl-N-propylpyrrolidinium bis(pentafluoroethyl)tetrafluorophosphate and/or N-methyl-N-propylpyrrolidinium hexafluorophosphate;

D) N-Methyl-N-pentylpyrrolidinium pentafluoroethyltrifluoroborate isolated or mixed with N-methyl-N-pentylpyrrolidinium (pentafluoroethyl)pentafluorophosphate and/or N-methyl-N-pentylpyrrolidinium bis(pentafluoroethyl)tetrafluorophosphate and/or N-methyl-N-pentylpyrrolidinium hexafluorophosphate;

E) N-Methyl-N-hexylpyrrolidinium pentafluoroethyltrifluoroborate isolated or mixed with N-methyl-N-hexylpyrrolidinium (pentafluoroethyl)pentafluorophosphate and/or N-methyl-N-hexylpyrrolidinium bis(pentafluoroethyl)tetrafluorophosphate and/or N-methyl-N-hexylpyrrolidinium hexafluorophosphate;

F) N-Methyl-N-heptylpyrrolidinium pentafluoroethyltrifluoroborate isolated or mixed with N-methyl-N-heptylpyrrolidinium (pentafluoroethyl)pentafluorophosphate and/or N-methyl-N-heptylpyrrolidinium bis(pentafluoroethyl)tetrafluorophosphate and/or N-methyl-N-heptylpyrrolidinium hexafluorophosphate;

G) N-Methyl-N-octylpyrrolidinium pentafluoroethyltrifluoroborate isolated or mixed with N-methyl-N-octylpyrrolidinium (pentafluoroethyl)pentafluorophosphate and/or N-methyl-N-octylpyrrolidinium bis(pentafluoroethyl)tetrafluorophosphate and/or N-methyl-N-octylpyrrolidinium hexafluorophosphate;

H) N-Methyl-N-nonylpyrrolidinium pentafluoroethyltrifluoroborate isolated or mixed with N-methyl-N-nonylpyrrolidinium (pentafluoroethyl)pentafluorophosphate and/or N-methyl-N-nonylpyrrolidinium bis(pentafluoroethyl)tetrafluorophosphate and/or N-methyl-N-nonylpyrrolidinium hexafluorophosphate;

I) N-Methyl-N-decylpyrrolidinium pentafluoroethyltrifluoroborate isolated or mixed with N-methyl-N-decylpyrrolidinium (pentafluoroethyl)pentafluorophosphate and/or N-methyl-N-decylpyrrolidinium bis(pentafluoroethyl)tetrafluorophosphate and/or N-methyl-N-decylpyrrolidinium hexafluorophosphate;

J) N,N-Dimethylpyrrolidinium pentafluoroethyltrifluoroborate isolated or mixed with N,N-dimethylpyrrolidinium (pentafluoroethyl)pentafluorophosphate and/or N,N-dimethylpyrrolidinium bis(pentafluoroethyl)tetrafluorophosphate and/or N,N-dimethylpyrrolidinium hexafluorophosphate;

K) N,N-Diethylpyrrolidinium pentafluoroethyltrifluoroborate isolated or mixed with N,N-diethylpyrrolidinium (pentafluoroethyl)pentafluorophosphate and/or N,N-diethylpyrrolidinium bis(pentafluoroethyl)tetrafluorophosphate and/or N,N-diethylpyrrolidinium hexafluorophosphate;

L) N,N-Di(i-propyl)pyrrolidinium pentafluoroethyltrifluoroborate isolated or mixed with N,N-di(i-propyl)pyrrolidinium (pentafluoroethyl)pentafluorophosphate and/or N,N-di(i-propyl)pyrrolidinium bis(pentafluoroethyl)tetrafluorophosphate and/or N,N-di(i-propyl)pyrrolidinium hexafluorophosphate;

M) N,N-Dipropylpyrrolidinium pentafluoroethyltrifluoroborate isolated or mixed with N,N-dipropylpyrrolidinium (pentafluoroethyl)pentafluorophosphate and/or N,N-dipropylpyrrolidinium bis(pentafluoroethyl)tetrafluorophosphate and/or N,N-dipropylpyrrolidinium hexafluorophosphate;

N) N,N-Dibutylpyrrolidinium pentafluoroethyltrifluoroborate isolated or mixed with N,N-dibutylpyrrolidinium (pentafluoroethyl)pentafluorophosphate and/or N,N-dibutylpyrrolidinium bis(pentafluoroethyl)tetrafluorophosphate and/or N,N-dibutylpyrrolidinium hexafluorophosphate;

O) N,N-Dipentylpyrrolidinium pentafluoroethyltrifluoroborate isolated or mixed with N,N-dipentylpyrrolidinium (pentafluoroethyl)pentafluorophosphate and/or N,N-dipentylpyrrolidinium bis(pentafluoroethyl)tetrafluorophosphate and/or N,N-dipentylpyrrolidinium hexafluorophosphate;

P) N,N-Dihexylpyrrolidinium pentafluoroethyltrifluoroborate isolated or mixed with N,N-dihexylpyrrolidinium (pentafluoroethyl)pentafluorophosphate and/or N,N-dihexylpyrrolidinium bis(pentafluoroethyl)tetrafluorophosphate and/or N,N-dihexylpyrrolidinium hexafluorophosphate;

Q) N,N-Diheptylpyrrolidinium pentafluoroethyltrifluoroborate isolated or mixed with N,N-diheptylpyrrolidinium (pentafluoroethyl)pentafluorophosphate and/or N,N-diheptylpyrrolidinium bis(pentafluoroethyl)tetrafluorophosphate and/or N,N-diheptylpyrrolidinium hexafluorophosphate;

R) N,N-Dioctylpyrrolidinium pentafluoroethyltrifluoroborate isolated or mixed with N,N-dioctylpyrrolidinium (pentafluoroethyl)pentafluorophosphate and/or N,N-dioctylpyrrolidinium bis(pentafluoroethyl)tetrafluorophosphate and/or N,N-dioctylpyrrolidinium hexafluorophosphate;

S) N,N-Dinonylpyrrolidinium pentafluoroethyltrifluoroborate isolated or mixed with N,N-dinonylpyrrolidinium (pentafluoroethyl)pentafluorophosphate and/or N,N-dinonylpyrrolidinium bis(pentafluoroethyl)tetrafluorophosphate and/or N,N-dinonylpyrrolidinium hexafluorophosphate;

T) N,N-Didecylpyrrolidinium pentafluoroethyltrifluoroborate isolated or mixed with N,N-didecylpyrrolidinium (pentafluoroethyl)pentafluorophosphate and/or N,N-didecylpyrrolidinium bis(pentafluoroethyl)tetrafluorophosphate and/or N,N-didecylpyrrolidinium hexafluorophosphate.

EXAMPLE 4

Synthesis of N-butylpyridinium pentafluoroethyltrifluoroborate

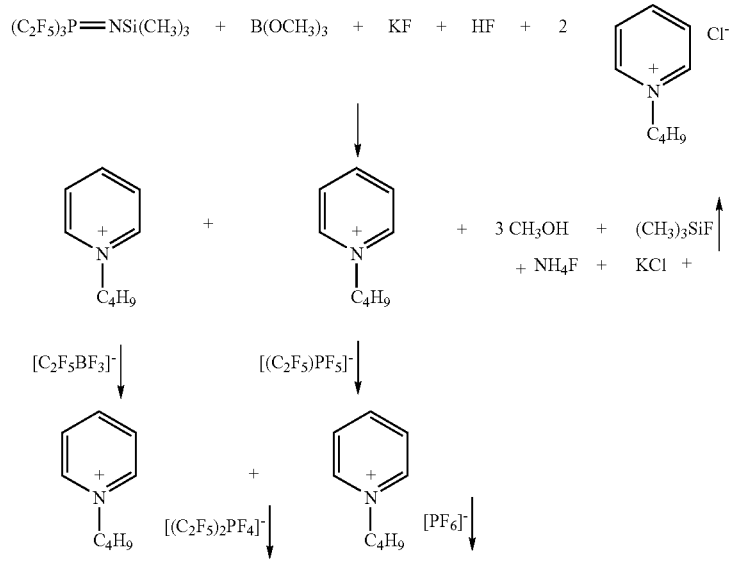

1.67 g (28.7 mmol) of spray-dried KF, 6.24 g (60.1 mmol) of methyl borate, 15.0 g (31.6 mmol) of N-trimethylsilyltris (pentafluoroethyl)phosphazene, 15 g (0.75 mol) of HF and 11.3 g (65.8 mmol) of N-butylpyridinium chloride are reacted analogously to Example 2.

The lower phase comprising the mixture of the salts N-butylpyridinium pentafluoroethyltrifluoroborate and N-butylpyridinium (pentafluoroethyl)pentafluorophosphate and/or N-butylpyridinium bis(pentafluoroethyl)tetrafluorophosphate and/or N-butylpyridinium hexafluorophosphate is separated from the aqueous phase and washed 10 times with 70 ml of water. After the water has been distilled off, the oily residue is again washed with water, and the phosphates are thus separated off.

Drying under reduced pressure at 7 Pa and 50° C. gives 7.4 g of N-butylpyridinium pentafluoroethyltrifluoroborate, corresponding to a yield of 79.8%.

$^{11}$B NMR: ppm (acetonitrile-D$_3$; external reference: BF$_3$.OEt$_2$): −0.59 tq; J$^1_{B,F}$=40.8 Hz; J$^2_{B,F}$=20.3 Hz.

$^{19}$F NMR: ppm (acetonitrile-D$_3$; internal reference: CCl$_3$F): −83.22 q (CF$_3$); −135.99 q (CF$_2$); −152.93 q,q (BF$_3$); $^1$J$_{B,F}$=41 Hz; $^2$J$_{B,F}$=19.6 Hz; $^4$J$_{F,F}$=4.6 Hz.

$^1$H NMR: ppm (acetonitrile-D$_3$; reference: TMS): 0.97 t (CH$_3$); 1.39 t,q (CH$_2$); 1.96 m (CH$_2$); 4.53 t (CH$_2$); 8.03 d,d (2CH); 8.51 t,t (CH); 8.70 d (2CH); $^3$J$_{H,H}$=7.4 Hz; $^3$J$_{H,H}$=7.6 Hz; $^3$J$_{H,H}$=7.8 Hz; $^3$J$_{H,H}$=6.9 Hz; $^3$J$_{H,H}$=5.5 Hz; $^4$J$_{H,H}$=1.3 Hz.

N-Butylpyridinium (pentafluoroethyl)pentafluorophosphate and the other phosphates can be isolated from the aqueous phase by known methods.

The following mixtures and also isolated compounds are prepared analogously to this example:

A) N-Methylpyridinium pentafluoroethyltrifluoroborate isolated or mixed with N-methylpyridinium (pentafluoroethyl)pentafluorophosphate and/or N-methylpyridinium bis(pentafluoroethyl)tetrafluorophosphate and/or N-methylpyridinium hexafluorophosphate;

B) N-Ethylpyridinium pentafluoroethyltrifluoroborate isolated or mixed with N-ethyl pyridinium (pentafluoroethyl)pentafluorophosphate and/or N-ethylpyridinium bis(pentafluoroethyl)tetrafluorophosphate and/or N-ethylpyridinium hexafluorophosphate;

C) N-(i-Propyl)pyridinium pentafluoroethyltrifluoroborate isolated or mixed with N-(i-propyl)pyridinium (pentafluoroethyl)pentafluorophosphate and/or N-(i-propyl)pyridinium bis(pentafluoroethyl)tetrafluorophosphate and/or N-(i-propyl)pyridinium hexafluorophosphate;

D) N-Propylpyridinium pentafluoroethyltrifluoroborate isolated or mixed with N-propylpyridinium (pentafluoroethyl)pentafluorophosphate and/or N-propylpyridinium bis(pentafluoroethyl)tetrafluorophosphate and/or N-propylpyridinium hexafluorophosphate;

E) N-Pentylpyridinium pentafluoroethyltrifluoroborate isolated or mixed with N-pentylpyridinium (pentafluoroethyl)pentafluorophosphate and/or N-pentylpyridinium bis(pentafluoroethyl)tetrafluorophosphate and/or N-pentylpyridinium hexafluorophosphate;

F) N-Hexylpyridinium pentafluoroethyltrifluoroborate isolated or mixed with N-hexylpyridinium (pentafluoroethyl)pentafluorophosphate and/or N-hexylpyridinium bis(pentafluoroethyl)tetrafluorophosphate and/or N-hexylpyridinium hexafluorophosphate;

G) N-Heptylpyridinium pentafluoroethyltrifluoroborate isolated or mixed with N-heptylpyridinium (pentafluoroethyl)pentafluorophosphate and/or N-heptylpyridinium bis(pentafluoroethyl)tetrafluorophosphate and/or N-heptylpyridinium hexafluorophosphate;

H) N-Octylpyridinium pentafluoroethyltrifluoroborate isolated or mixed with N-octylpyridinium (pentafluoroethyl)pentafluorophosphate and/or N-octylpyridinium bis(pentafluoroethyl)tetrafluorophosphate and/or N-octylpyridinium hexafluorophosphate;

I) N-Nonylpyridinium pentafluoroethyltrifluoroborate isolated or mixed with N-nonylpyridinium (pentafluoroethyl)pentafluorophosphate and/or N-nonylpyridinium bis(pentafluoroethyl)tetrafluorophosphate and/or N-nonylpyridinium hexafluorophosphate;

J) N-Decylpyridinium pentafluoroethyltrifluoroborate isolated or mixed with N-decylpyridinium (pentafluoroethyl)pentafluorophosphate and/or N-decylpyridinium bis(pentafluoroethyl)tetrafluorophosphate and/or N-decylpyridinium hexafluorophosphate;

K) N-Methyl-4-methylpyridinium pentafluoroethyltrifluoroborate isolated or mixed with N-methyl-4-methylpyridinium (pentafluoroethyl)pentafluorophosphate and/or N-methyl-4-methylpyridinium bis(pentafluoroethyl)tetrafluorophosphate and/or N-methyl-4-methylpyridinium hexafluorophosphate;

L) N-Ethyl-4-methylpyridinium pentafluoroethyltrifluoroborate isolated or mixed with N-ethyl-4-methylpyridinium (pentafluoroethyl)pentafluorophosphate and/or N-ethyl-4-methylpyridinium bis(pentafluoroethyl)tetrafluorophosphate and/or N-ethyl-4-methylpyridinium hexafluorophosphate;

M) N-(i-Propyl)-4-methylpyridinium pentafluoroethyltrifluoroborate isolated or mixed with N-(i-propyl)-4-methylpyridinium (pentafluoroethyl)pentafluorophosphate and/or N-(i-propyl)-4-methylpyridinium bis(pentafluoroethyl)tetrafluorophosphate and/or N-(i-propyl)-4-methylpyridinium hexafluorophosphate;

N) N-Propyl-4-methylpyridinium pentafluoroethyltrifluoroborate isolated or mixed with N-propyl-4-methylpyridinium (pentafluoroethyl)pentafluorophosphate and/or N-propyl-4-methylpyridinium bis(pentafluoroethyl)tetrafluorophosphate and/or N-propyl-4-methylpyridinium hexafluorophosphate;

O) N-Butyl-4-methylpyridinium pentafluoroethyltrifluoroborate isolated or mixed with N-butyl-4-methylpyridinium (pentafluoroethyl)pentafluorophosphate and/or N-butyl-4-methylpyridinium bis(pentafluoroethyl)tetrafluorophosphate and/or N-butyl-4-methylpyridinium hexafluorophosphate;

P) N-Pentyl-4-methylpyridinium pentafluoroethyltrifluoroborate isolated or mixed with N-pentyl-4-methylpyridinium (pentafluoroethyl)pentafluorophosphate and/or N-pentyl-4-methylpyridinium bis(pentafluoroethyl)tetrafluorophosphate and/or N-pentyl-4-methylpyridinium hexafluorophosphate;

Q) N-Hexyl-4-methylpyridinium pentafluoroethyltrifluoroborate isolated or mixed with N-hexyl-4-methylpyridinium (pentafluoroethyl)pentafluorophosphate and/or N-hexyl-4-methylpyridinium bis(pentafluoroethyl)tetrafluorophosphate and/or N-hexyl-4-methylpyridinium hexafluorophosphate;

R) N-Heptyl-4-methylpyridinium pentafluoroethyltrifluoroborate isolated or mixed with N-heptyl-4-methylpyridinium (pentafluoroethyl)pentafluorophosphate and/or N-heptyl-4-methylpyridinium bis(pentafluoroethyl)tetrafluorophosphate and/or N-heptyl-4-methylpyridinium hexafluorophosphate;

S) N-Octyl-4-methylpyridinium pentafluoroethyltrifluoroborate isolated or mixed with N-octyl-4-methylpyridinium (pentafluoroethyl)pentafluorophosphate and/or N-octyl-4-methylpyridinium bis(pentafluoroethyl)tetrafluorophosphate and/or N-octyl-4-methylpyridinium hexafluorophosphate;

T) N-Nonyl-4-methylpyridinium pentafluoroethyltrifluoroborate isolated or mixed with N-nonyl-4-methylpyridinium (pentafluoroethyl)pentafluorophosphate and/or N-nonyl-4-methylpyridinium bis(pentafluoroethyl)tetrafluorophosphate and/or N-nonyl-4-methylpyridinium hexafluorophosphate;

U) N-Decyl-4-methylpyridinium pentafluoroethyltrifluoroborate isolated or mixed with N-decyl-4-methylpyridinium (pentafluoroethyl)pentafluorophosphate and/or N-decyl-4-methylpyridinium bis(pentafluoroethyl)tetrafluorophosphate and/or N-decyl-4-methylpyridinium hexafluorophosphate;

V) N-Methyl-3-methylpyridinium pentafluoroethyltrifluoroborate isolated or mixed with N-methyl-3-methylpyridinium (pentafluoroethyl)pentafluorophosphate and/or N-methyl-3-methylpyridinium bis(pentafluoroethyl)tetrafluorophosphate and/or N-methyl-3-methylpyridinium hexafluorophosphate;

W) N-Ethyl-3-methylpyridinium pentafluoroethyltrifluoroborate isolated or mixed with N-ethyl-3-methylpyridinium (pentafluoroethyl)pentafluorophosphate and/or N-ethyl-3-methylpyridinium bis(pentafluoroethyl)tetrafluorophosphate and/or N-ethyl-3-methylpyridinium hexafluorophosphate;

X) N-(i-Propyl)-3-methylpyridinium pentafluoroethyltrifluoroborate isolated or mixed with N-(i-propyl)-3-methylpyridinium (pentafluoroethyl)pentafluorophosphate and/or N-(i-propyl)-3-methylpyridinium bis(pentafluoroethyl)tetrafluorophosphate and/or N-(i-propyl)-3-methylpyridinium hexafluorophosphate;

Y) N-Propyl-3-methylpyridinium pentafluoroethyltrifluoroborate isolated or mixed with N-propyl-3-methylpyridinium (pentafluoroethyl)pentafluorophosphate and/or N-propyl-3-methylpyridinium bis(pentafluoroethyl)tetrafluorophosphate and/or N-propyl-3-methylpyridinium hexafluorophosphate;

Z) N-Butyl-3-methylpyridinium pentafluoroethyltrifluoroborate isolated or mixed with N-butyl-3-methylpyridinium (pentafluoroethyl)pentafluorophosphate and/or N-butyl-3-methylpyridinium bis(pentafluoroethyl)tetrafluorophosphate and/or N-butyl-3-methylpyridinium hexafluorophosphate;

A1) N-Pentyl-3-methylpyridinium pentafluoroethyltrifluoroborate isolated or mixed with N-pentyl-3-methylpyridinium (pentafluoroethyl)pentafluorophosphate and/or N-pentyl-3-methylpyridinium bis(pentafluoroethyl)tetrafluorophosphate and/or N-pentyl-3-methylpyridinium hexafluorophosphate;

B1) N-Hexyl-3-methylpyridinium pentafluoroethyltrifluoroborate isolated or mixed with N-hexyl-3-methylpyridinium (pentafluoroethyl)pentafluorophosphate and/or N-hexyl-3-methylpyridinium bis(pentafluoroethyl)tetrafluorophosphate and/or N-hexyl-3-methylpyridinium hexafluorophosphate;

C1) N-Heptyl-3-methylpyridinium pentafluoroethyltrifluoroborate isolated or mixed with N-heptyl-3-methylpyridinium (pentafluoroethyl)pentafluorophosphate and/or N-heptyl-3-methylpyridinium bis(pentafluoroethyl)tetrafluorophosphate and/or N-heptyl-3-methylpyridinium hexafluorophosphate;

D1) N-Octyl-3-methylpyridinium pentafluoroethyltrifluoroborate isolated or mixed with N-octyl-3-methylpyridinium (pentafluoroethyl)pentafluorophosphate and/or N-octyl-3-methylpyridinium bis(pentafluoroethyl)tetrafluorophosphate and/or N-octyl-3-methylpyridinium hexafluorophosphate;

E1) N-Nonyl-3-methylpyridinium pentafluoroethyltrifluoroborate isolated or mixed with N-nonyl-3-methylpyridinium (pentafluoroethyl)pentafluorophosphate and/or N-nonyl-3-methylpyridinium bis(pentafluoroethyl)tetrafluorophosphate and/or N-nonyl-3-methylpyridinium hexafluorophosphate;

F1) N-Decyl-3-methylpyridinium pentafluoroethyltrifluoroborate isolated or mixed with N-decyl-3-methylpyridinium (pentafluoroethyl)pentafluorophosphate and/or N-decyl-3-methylpyridinium bis(pentafluoroethyl)tetrafluorophosphate and/or N-decyl-3-methylpyridinium hexafluorophosphate.

EXAMPLE 5

Viscosity Data

Table 1 below shows viscosity data. The viscosity was determined using an SVM3000 viscometer from Anton Paar, Austria, with the standard procedure as described in the material accompanying the viscometer being carried out.

TABLE 1

| | Viscosity data | | | |
|---|---|---|---|---|
| Compound | Viscosity, cP (mPa · s) 20° C. | 40° C. | 60° C. | 80° C. |
| 1-Butyl-3-methylimidazolium (pentafluoroethyl)trifluoroborate | 70 | 32 | 18 | 11 |
| 1-Butylpyridinium (pentafluoroethyl)trifluoroborate | 86 | 37 | 19 | 11 |

EXAMPLE 6

Cyclic Voltamogram, FIG. 1

The electrochemical stability of N-butyl-N-methylpyrrolidinium (pentafluoroethyl)trifluoroborate was measured using an ECO-Chemie Autolab TGSTAT 30 potentiostat.

Working electrode: glassy carbon

Counterelectrode: platinum disc

Reference electrode: Ag/Ag$^+$

Scan rate: 20 mV/S

N-Butyl-N-methylpyrrolidinium (pentafluoroethyl)trifluoroborate is dissolved in acetonitrile to give a 0.5 molar solution, and the solution is measured at room temperature under argon in a glove box.

The cyclic voltamogram in FIG. 1 shows that the compound has high electrochemical stability in the range from −3 to +4 V (zero is the reference for E° of ferrocene).

EXAMPLE 7

Thermal Stability

Table 2 below lists data showing the rate at which decomposition of the perfluoroalkylborate compound to give tetrafluoroborate compounds takes place. These data clearly show that trifluoromethyltrifluoroborate salts are not thermally stable.

The decomposition rate was determined by heating the samples to 150° C. and measuring them by $^{19}$F NMR spectroscopy.

TABLE 2

| Compound | Decomposition rate to [BF$_4$]$^-$ 150° C., 1 hour | 150° C., 5 hours |
|---|---|---|
| 1-Butyl-3-methylimidazolium (pentafluoroethyl)trifluoroborate | 0 | 0 |
| 1-Butyl-3-methylimidazolium (trifluoromethyl)trifluoroborate | about 1 mol % | 60 mol % |

EXAMPLE 8

Synthesis of 2,2,3,3,3-pentafluoro-1-phenylpropan-1-ol (C$_2$F$_5$)$_3$P=NSi(CH$_3$)$_3$+(CH$_3$)$_4$NF+C$_6$H$_5$C(O)H→C$_6$H$_5$CH(OH)C$_2$F$_5$ 1.59 g (16.1 mmol) of tetramethylammonium fluoride and 8.54 g (80.5 mmol) of benzaldehyde are dissolved in 20 ml of dry 1,2-dimethoxyethane. 8.4 g (17.7 mmol) of N-trimethylsilyltris(pentafluoroethyl)phosphazene are added dropwise to this solution at a bath temperature of −30° C. under a protective gas. The reaction mixture is slowly warmed to room temperature, and the solvent is distilled off. The residue is diluted with an aqueous NaOH solution (4.1 g of NaOH in 40 ml of water), and the aqueous phase is extracted twice with 40 ml of diethyl ether. The extract is washed with a 0.1M hydrochloric acid and water and dried over MgSO$_4$. The solvent diethyl ether is distilled off, and the residue is subjected to fractional distillation, where the fraction at 110-115° C. corresponds to the compound 2,2,3,3,3-pentafluoro-1-phenylpropan-1-ol (2.3 g). The yield is 63.2%.

$^{19}$F NMR: ppm (acetonitrile-D$_3$; reference: CCl$_3$F): −80.63 s (CF$_3$); −119.19 d,d (ABX system, CF$_A$); −129.19 d,d (ABX system, CF$_B$); J$_{A,B}$=274 Hz; $^3$J$_{H,F(A)}$=6.5 Hz; $^3$J$_{H,F(B)}$=19.1 Hz.

$^1$H NMR: ppm (acetonitrile-D$_3$; reference: TMS): 4.61 br. s (OH), 5.26 d,d (CH), 7.41-7.56 (C$_6$H$_5$).

The NMR data and the boiling point correspond to the data from the literature.

EXAMPLE 9

Synthesis of 2,2,3,3,3-pentafluoro-1,1-diphenylpropan-1-ol 2.23 g (23.9 mmol) of tetramethylammonium fluoride and 8.41 g (46.2 mmol) of benzophenone are dissolved in 20 ml of dry 1,2-dimethoxyethane. 12.32 g (25.9 mmol) of N-trimethylsilyltris(pentafluoroethyl)phosphazene are added dropwise to this solution at a bath temperature of −30° C. under a protective gas. The reaction mixture is slowly warmed to room temperature, and the precipitate is filtered off under a protective gas. After washing a number of times with diethyl ether, it is dried under reduced pressure. The residue is furthermore treated with 20 ml of a 20% hydrochloric acid, and the aqueous phase is extracted with diethyl ether. The organic phase is washed with a 0.1M aqueous sodium hydrogencarbonate solution and dried over MgSO$_4$. The solvent diethyl ether is distilled off, giving 5.7 g of 2,2,3,3,3-pentafluoro-1,1-diphenylpropan-1-ol, corresponding to a yield of 78.9%.

Melting point: 82-83° C.

$^{19}$F NMR: ppm (acetonitrile-D$_3$; reference: CCl$_3$F): −76.32 t (CF$_3$); −114.71 q (CF$_2$); $^3$J$_{F,F}$=0.9 Hz.

$^1$H NMR: ppm (acetonitrile-D$_3$; reference: TMS): 5.03 br. s (OH), 7.31-7.42 (6H, C$_6$H$_5$), 7.58-7.63 (4H, C$_6$H$_5$).

The invention claimed is:

1. A compound of the formula Ia

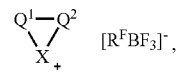   [R$^F$BF$_3$]$^-$,   I in which

X denote N(R$^1$)$_2$,

-Q$^1$-Q$^2$- denotes —CHR$^3$—CHR$^4$—CHR$^5$—CHR$^6$,

R$^1$ in each case, independently of one another, denotes alkyl having 1-10 C atoms or —(CH$_2$)—R$^{11}$, R$^3$-R$^6$ denote hydrogen or alkyl having 1-10 C atoms, R$^{11}$ denotes perfluorinated or partially fluorinated alkyl having 1-8 and R$^F$ denotes perfluorinated alkyl having 2-8 C atoms.

2. Compounds according to claim 1, wherein the substituents R$^1$ are different.

3. A compound according to claim 1, wherein R$^F$ denotes perfluoroethyl, perfluoropropyl or perfluorobutyl.

4. A compound according to claim 1 which is:

N-methyl-N-butylpyrrolidinium pentafluoroethyltrifluoroborate,

N-methyl-N-hexylpyrrolidinium pentafluoroethyltrifluoroborate, or

N-methyl-N-octylpyrrolidinium pentafluoroethyltrifluoroborate.

5. A process for the preparation of a compound according to claim 1, comprising reacting a compound of the formula II (R$^F$)$_3$P=NSi(R$^{12}$)$_3$   II, in which R$^F$ in each case, independently of one another, denotes perfluorinated alkyl having 2-8 C atoms, and R$^{12}$ in each case, independently of one another, denotes alkyl having 1-8 C atoms, alkoxy having 1-8 C atoms, cycloalkyl having 3-7 C atoms, halogen or aryl, with a fluoride of the formula III

MF   III, in which

M is ammonium, alkali metal or alkaline earth metal or a metal from group 11 or 12, and a boric acid ester of the formula IV

B(OR$^{13}$)$_3$   IV, in which

R$^{13}$ in each case, independently of one another, denotes alkyl having 1-8 C atoms or aryl, and reacting a resultant salt of formula V

M[R$^F$B(OR$^{13}$)$_3$]   V, in which M, R$^F$ and R$^{13}$ have one of the above-mentioned meanings, with HF, and reacting a resultant salt of formula VI $$M[R^FBF_3] \quad \text{VI,}$$

in which $R^F$ is as defined above,
with a compound of the formula VII

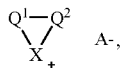   VII in which X and -Q$^1$-Q$^2$- are as defined for the formula I in claim 1, and A$^-$ denotes alkylsulfate, alkylsulfonate, trifluoromethanesulfonate, tetrafluoroborate, acetate, trifluoroacetate, bis(perfluoroalkyl)phosphinate, F$^-$, HF$_2^-$, Cl$^-$, Br$^-$ or I$^-$.

6. A mixture of at least one salt of the formula I with at least one salt of the formulae VIII, IX and X,

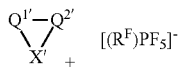  [R$^F$BF$_3$]$^-$,   I

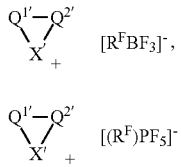  [(R$^F$)PF$_5$]$^-$   VIII

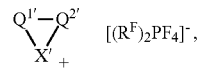  [(R$^F$)$_2$PF$_4$]$^-$,   IX

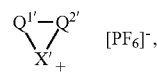  [PF$_6$]$^-$,   X where
X, -Q$^1$-Q$^2$- and R$^F$ have the meaning indicated in claim 1,
X' is NR$^1$ or N(R$^1$)$_2$,
Q$^{1'}$-Q$^{2'}$- denotes —CHR$^3$—CHR$^4$—CHR$^5$—CHR$^6$,
—CR$^2$=CR$^3$—CR$^4$=CR$^5$—CR$^6$= or
—CR$^7$=CR$^8$—NR$^{10}$—CR$^9$=,
R$^2$-R$^6$ denote hydrogen or alkyl having 1-10 C atoms,
R$^7$-R$^9$ denote hydrogen, alkyl having 1-10 C atoms or aryl,
R$^{10}$ denotes alkyl having 2-8 C atoms or —(CH$_2$)—R$^{11}$,
aryl
   denotes phenyl, perfluorinated phenyl, or phenyl or perfluorinated phenyl which is substituted by alkyl having 1-8 C atoms.

7. A mixture according to claim 6, comprising 50-75 mol % of compounds of the formula I and 25-50 mol % of compounds of the formulae VIII, IX and/or X.

8. An ionic liquid containing a compound according to claim 1.

* * * * *